US011879830B2

(12) United States Patent
Xiong et al.

(10) Patent No.: US 11,879,830 B2
(45) Date of Patent: Jan. 23, 2024

(54) QUANTITATIVE LARGE AREA BINDING SENSOR FOR DETECTING BIOMARKERS

(71) Applicant: Arizona Board of Regents on Behalf of the University of Arizona, Tucson, AZ (US)

(72) Inventors: Zhen Xiong, Tucson, AZ (US); Euan McLeod, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 471 days.

(21) Appl. No.: 17/281,221

(22) PCT Filed: Sep. 27, 2019

(86) PCT No.: PCT/US2019/053530
§ 371 (c)(1),
(2) Date: Mar. 29, 2021

(87) PCT Pub. No.: WO2020/139430
PCT Pub. Date: Jul. 2, 2020

(65) Prior Publication Data
US 2021/0396647 A1     Dec. 23, 2021

Related U.S. Application Data

(60) Provisional application No. 62/738,602, filed on Sep. 28, 2018.

(51) Int. Cl.
*G06K 9/00*     (2022.01)
*G01N 15/14*     (2006.01)
(Continued)

(52) U.S. Cl.
CPC ..... *G01N 15/1475* (2013.01); *G01N 15/1434* (2013.01); *G01N 15/1484* (2013.01);
(Continued)

(58) Field of Classification Search
CPC ........... G01N 15/1475; G01N 15/1434; G01N 15/1484; G01N 33/54313;
(Continued)

(56) References Cited

U.S. PATENT DOCUMENTS 10,989,724 B1 *    4/2021    Holmes ................. G01N 35/02
2012/0098950 A1     4/2012    Zheng et al.
(Continued)

FOREIGN PATENT DOCUMENTS

CN     105960463 A   *   9/2016      ........ B01L 3/502753
CN     109967143 A   *   7/2019
(Continued)

OTHER PUBLICATIONS

Lai, et al., "Wave front-reconstruction by means of phase-shifting digital in-line holography." Optics communications 173, 1-6 (2000): 155-160. [online]<https://www.sciencedirect.com/science/article/pii/S0030401899006252>.
(Continued)

*Primary Examiner* — Xin Jia
(74) *Attorney, Agent, or Firm* — George R. McGuire

(57) ABSTRACT

An imaging system and method for detecting a target in a sample. The imaging system includes a lens-free holographic microscope having a light source in a first plane spaced above an image sensor. The image sensor extends in a second plane. The system also includes a microfluidic chip positioned between the light source and the image sensor. The microfluidic chip extends in a third plane, which is parallel to the second plane. There is at least one chamber in the microfluidic chip configured to receive a sample solution with a target. The system also has a plurality of functionalized beads positioned within the at least one chamber in the microfluidic chip. Any two of the plurality of function-
(Continued)

alized beads have an affinity for binding together when exposed to the target in the sample solution.

20 Claims, 12 Drawing Sheets

(51) Int. Cl.
  *G01N 33/543* (2006.01)
  *G01N 15/00* (2006.01)
  *G01N 15/10* (2006.01)

(52) U.S. Cl.
  CPC .......... *G01N 33/54313* (2013.01); *G01N 2015/0038* (2013.01); *G01N 2015/0092* (2013.01); *G01N 2015/1006* (2013.01); *G01N 2015/1454* (2013.01); *G01N 2015/1486* (2013.01)

(58) Field of Classification Search
  CPC ... G01N 2015/0038; G01N 2015/0092; G01N 2015/1006; G01N 2015/1454; G01N 2015/1486; G01N 33/54366
  See application file for complete search history.

(56) References Cited

U.S. PATENT DOCUMENTS

| | | |
|---|---|---|
| 2013/0222547 A1 | 8/2013 | Van Rooyen et al. |
| 2013/0310270 A1 | 11/2013 | Colle et al. |
| 2015/0056607 A1 | 2/2015 | Jooris et al. |
| 2017/0168285 A1 | 6/2017 | Ozcan et al. |
| 2017/0270388 A1 | 9/2017 | Vercruysse |

FOREIGN PATENT DOCUMENTS

| | | | |
|---|---|---|---|
| WO | 2002023154 A2 | 3/2002 | |
| WO | WO-2014127379 A1 * | 8/2014 | .............. B01L 3/021 |
| WO | WO-2019236569 A1 * | 12/2019 | ........ B01L 3/502715 |

OTHER PUBLICATIONS

International Search Report and Written Opinion of PCT Application No. PCT/US2019/053530 dated Jun. 3, 2020, 9 pages.

* cited by examiner (a) Bead loading (device fabrication)

(b) Post-fabrication, pre-use (c) Flow sample and incubate
Beads & target analytes diffuse (d) Assay ready for quantification
Beads sandwich target analyte(s)

QUANTITATIVE LARGE AREA BINDING SENSOR FOR DETECTING BIOMARKERS

CROSS-REFERENCE TO RELATED APPLICATIONS

This application is the United States National Stage Application of International Application No. PCT/US19/053530, filed Sep. 27, 2019, which claims priority to U.S. Provisional Patent Application Ser. No. 62/738,602 filed on Sep. 28, 2018 and entitled "Quantitative Large Area Binding Sensor for Detecting Biomarkers," the entirety of each of which is incorporated herein by reference.

BACKGROUND OF THE INVENTION

1. Field of the Invention

The present invention is directed generally to optical imaging and, more particularly, to an imaging system for the detection of a target.

2. Description of Related Art

Biosensors have numerous applications in various fields such as disease screening and detection, environmental monitoring, and food processing control. Maximum sensitivity biosensors have the capability of detecting individual analyte particles, which can include human cells, bacteria, viruses, exosomes, proteins, or DNA. It is often a challenge to individually detect such small particles. It is also desirable for biosensors to be compact and cost-effective to enable point-of-care use. Point-of-care biosensors have gained significant attention due to their immediacy, convenience, and accessibility in medical testing.

The ideal biosensors for point-of-care use possess traits of sensitivity, selectivity, dynamic range, multiple analyte sensing (multiplexing), low sample volume requirements, simple and rapid protocols, cost-effectiveness, and compactness. Sensitivity is needed to measure low concentrations of target analytes as biomarkers for the early detection of disease. Selectivity ensures the correct target analyte biomarker is detected, rather than other spurious molecules. Dynamic range is important for a test to be relevant for patients who may have a range of biomarker levels that correspond to different stages of disease. Multiplexing allows multiple, distinct biomarkers to be quantified using a single test. Small sample volumes minimize invasiveness and reduce diffusion time. Simple protocols can also shorten testing times and reduce the probability of procedural errors, decreasing the training burden and reducing the cost per test. Finally, cost-effectiveness and compactness often go hand-in-hand and enable field-portable and point-of-care testing that is particularly relevant for environmental sensing, personalized (precision) medicine, and global health applications in regions where it is infeasible and/or prohibitively expensive to send samples to central laboratories for testing. While there are currently many biosensing approaches, there is no single technology that meets all the criteria for optimizing point-of-care use.

Therefore, there is a need for a biosensor and biosensing methods that are optimized for point-of-care use.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Lens-free holographic microscopy (LFHM) can be used to image objects such as viruses and cells, as well as non-biological structures. It provides an ultra-large field-of-view (>20 mm$^2$) with sub-micron resolution, which are key enablers of high dynamic range and extreme multiplexing. Furthermore, LFHM is amendable to compact and cost-effective field-portable devices. The approach described herein can image and enumerate anywhere from a single bead-pair up to ~10$^5$ bead pairs. This ability, provided by high resolution and ultra large field-of-view of LFHM, simultaneously enables high sensitivity, high dynamic range, and multiplexing. Furthermore, the proposed microfluidic approach operates with ultra-small (~0.1 µL) volumes, which minimizes invasiveness, as well as reduces diffusion lengths, thus speeding reaction and sensing times. Sample analysis is designed to be done in a single flow step with no washing steps, which keeps protocols simple and minimizes analysis time. Developing biosensing approaches that combine all of these aspects will ensure devices that can be feasibly translated from the laboratory into the clinic and the field.

Embodiments of the present invention are directed to an imaging system and method for detecting a target in a sample. According to one aspect, the imaging system includes a lens-free holographic microscope having a light source in a first plane spaced above an image sensor. The image sensor extends in a second plane. The system also includes a microfluidic chip positioned between the light source and the image sensor. The microfluidic chip extends in a third plane, which is parallel to the second plane. There is at least one chamber in the microfluidic chip configured to receive a sample solution with a target. The system also has a plurality of functionalized beads positioned within the at least one chamber in the microfluidic chip. Any two of the plurality of functionalized beads have an affinity for binding together when exposed to the target in the sample solution.

According to another aspect, the present invention is a method for determining the presence of a target in a sample. The method includes the steps of: (i) providing an imaging system including a lens-free holographic microscope comprising a light source in a first plane spaced above an image sensor, wherein the image sensor extends in a second plane, a microfluidic chip positioned between the light source and the image sensor, wherein the microfluidic chip extends in a third plane, which is parallel to the second plane, at least one chamber in the microfluidic chip, and a plurality of functionalized beads, any two of the plurality of functionalized beads with an affinity for binding together when exposed to the target, wherein the plurality of functionalized beads are positioned within the at least one chamber in the microfluidic chip; (ii) adding the sample to the at least one chamber in the microfluidic chip; (iii) directing the light source toward the microfluidic chip and the image sensor; (iv)

capturing, via the image sensor, an interference pattern generated by light scattered by the sample; (v) generating a hologram image based on the interference pattern; and (vi) reconstructing the hologram image to generate an in-focus image.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
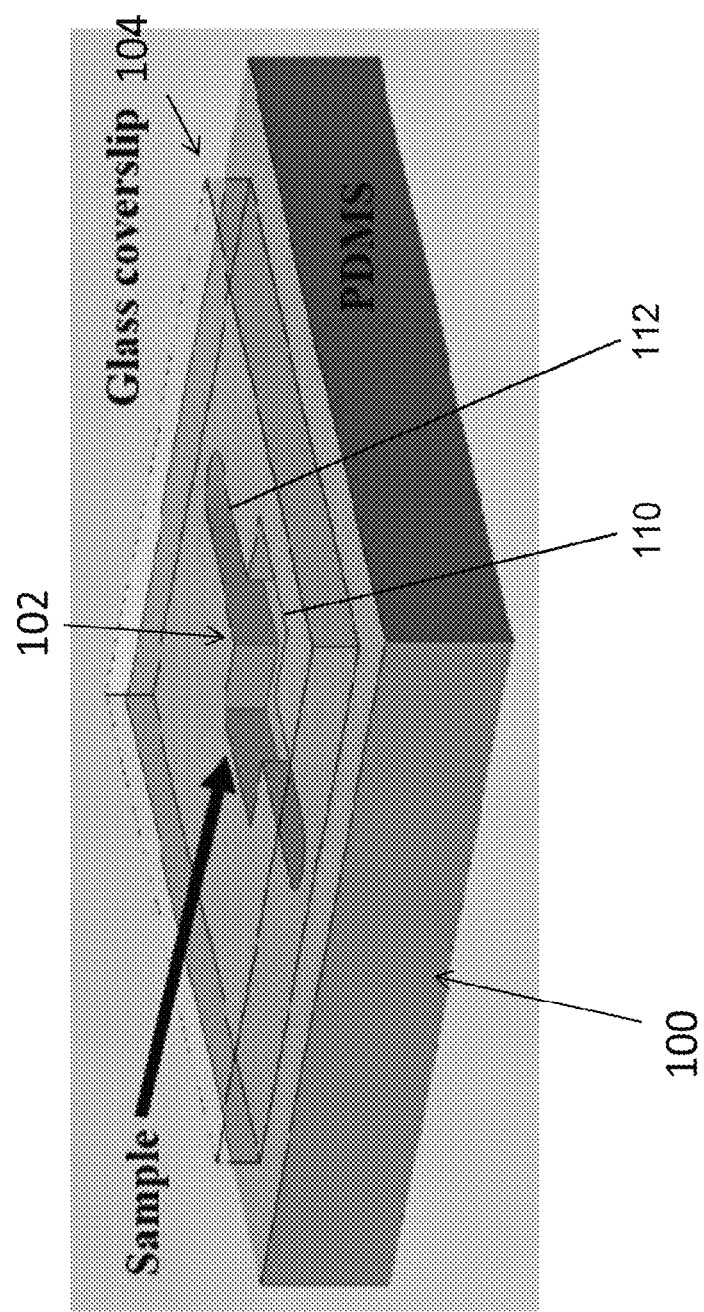
FIG. 1 is a perspective view schematic representation of a microfluidic chip, according to an embodiment.

Referring now to the figures, wherein like reference numerals refer to like parts throughout, FIG. 1 shows a perspective view schematic representation of a microfluidic chip 100, according to an embodiment. In a preferred embodiment, the microfluidic chip 100 is composed of PDMS; however, any other similar suitable material can be used. The microfluidic chip 100 comprises a sample chamber 102. In the depicted embodiment, the sample chamber 102 is cross-shaped or t-shaped with a rectangular central area 110 and a channel 112 extending therethrough.

Still referring to FIG. 1, the microfluidic chip 100 also comprises a cover 104. In the depicted embodiment, the cover 104 is a glass coverslip, as shown. The cover 104 can be any transparent material that allows for light illumination of the microfluidic chip 100. In use, a sample is placed into the sample chamber 102 and the sample is observed with a lens-free holographic microscope (LFHM). LFHM can be used to detect microscale targets (e.g., bacteria and cells) and nanoscale targets (e.g., viruses, DNA strands, and cancer biomarkers), as will be discussed below. Nanoscale targets can be observed with the use of functionalized microsphere beads. Thus, the target molecule can include (but are not limited to) pathogens (e.g., *E. coli, Salmonella, Listeria*), protein molecules, such as cytokine molecules (which are markers of various diseases, including graft vs. host disease), DNA, and RNA.

Figure 2:
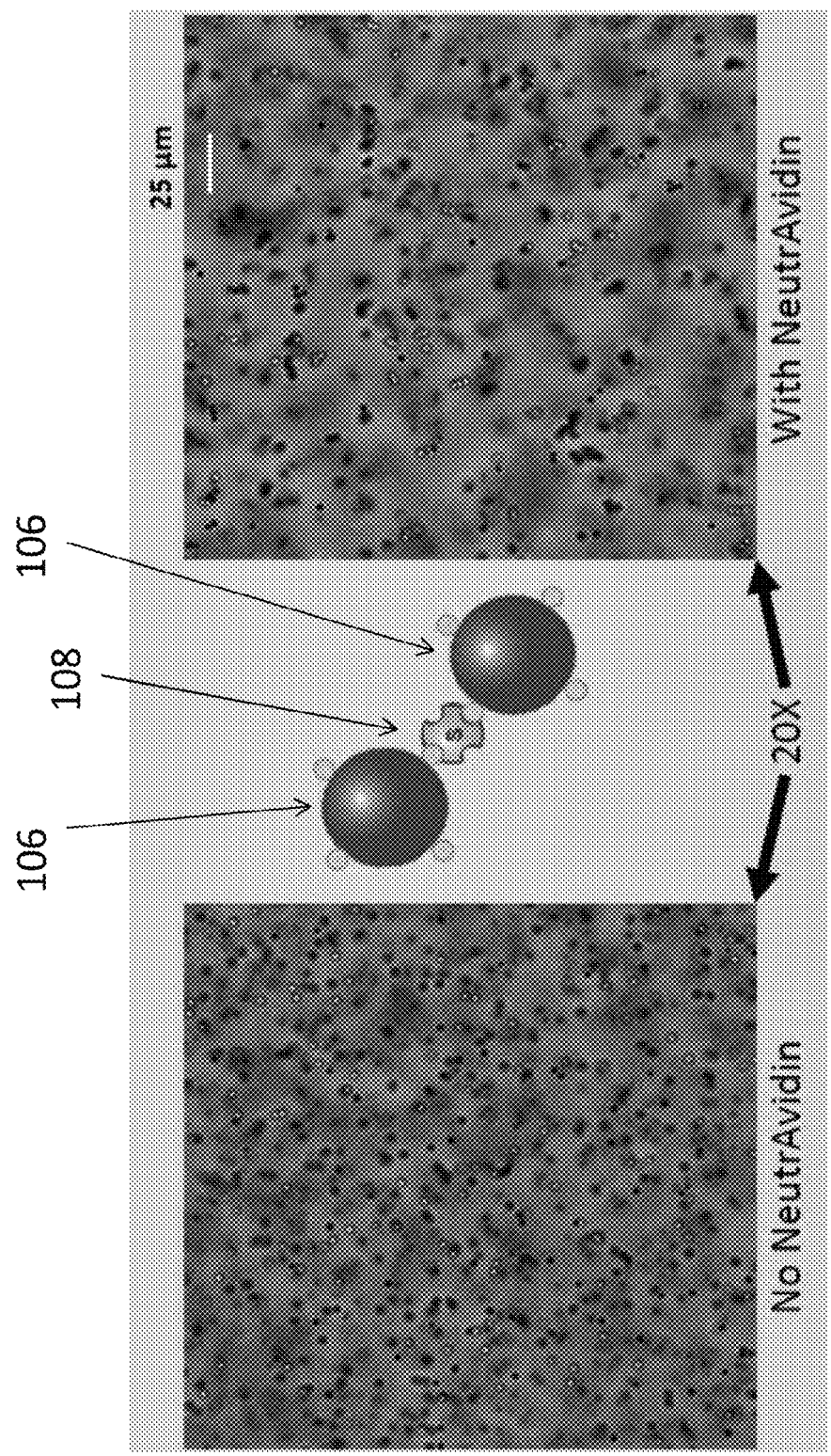
FIG. 2 is a diagrammatic representation of functionalized microsphere beads in binding interactions.

Turning now to FIG. 2, there is shown diagrammatic representation of functionalized microsphere beads 106 in binding interactions. The functionalized beads 106 can be composed of dielectric materials (e.g., polystyrene) or metals and can be either spherical or nonspherical (e.g., rod-shaped). The functionalized beads 106 can be functionalized using one or more of the following capture agents: antibodies, protein aptamers, DNA aptamers, and RNA aptamers. In an example, as shown in FIG. 2, biotin-coated microspheres 106 are used for the detection of NeutrAvidin 108 concentrations. In other words, the beads 106 can be used to detect concentrations of nanoscale targets in solutions. Optical tweezers can be used to manufacture or position the beads 106 inside sample-holding devices, such as the microfluidic chip 100 (as discussed in detail below). LFHM can be well-suited for detecting targets with beads 206 because they have high-speed image sensors and fast switchable light sources for imaging the motion of microbeads in solution using super-resolution.

Figure 3:
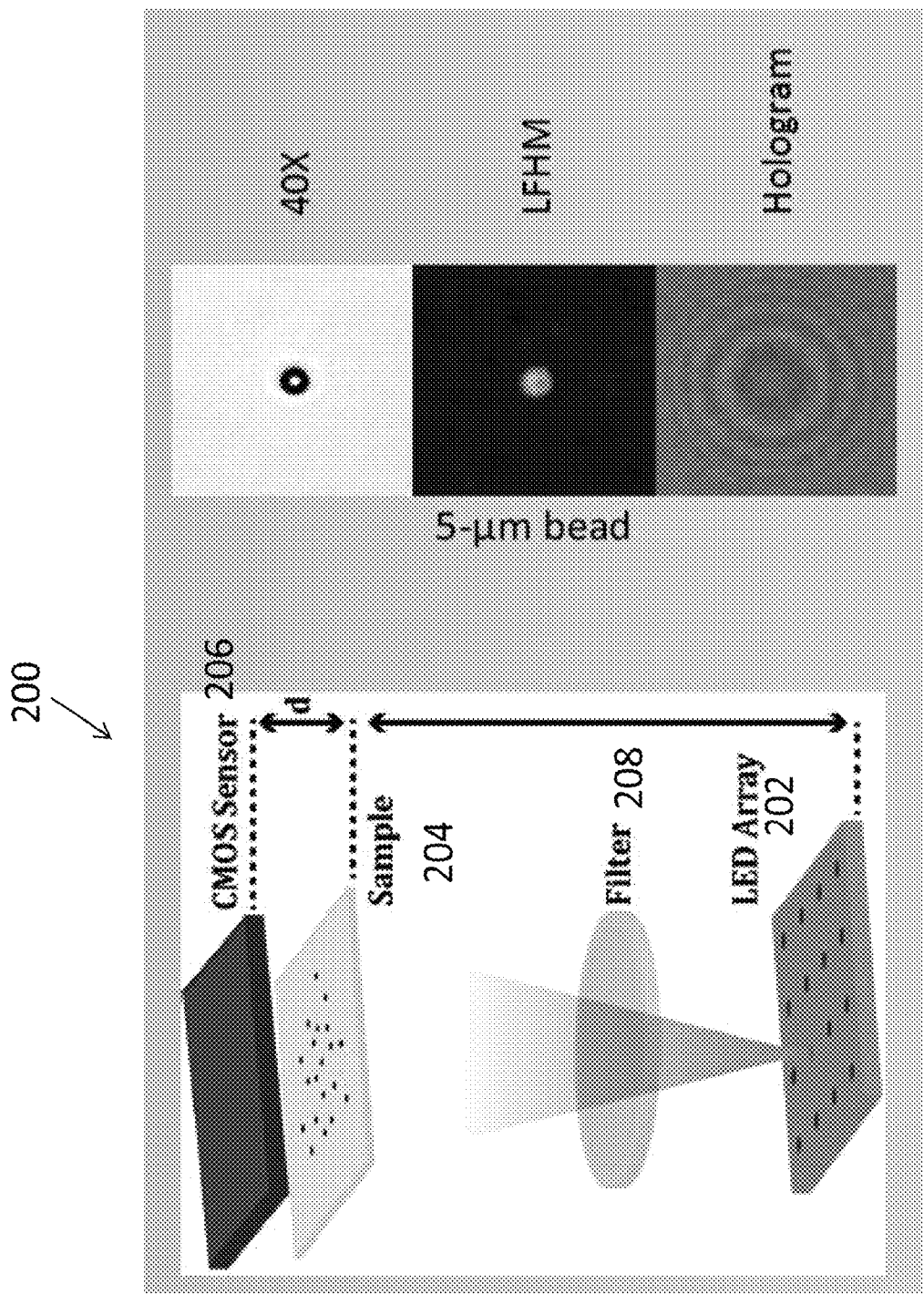
FIG. 3 is a schematic representation of a LFHM system, according to an embodiment.

Referring now to FIG. 3, there is shown a schematic representation of a LFHM system 200, according to an embodiment. The LFHM system 200 includes an LED array 202 to illuminate the sample 204 (in one large sample chamber 102). (Note, the sample 204 can be the microfluidic chip 100 of FIG. 1 with a sample in the chamber 102). The embodiment of the LFHM system 200 with one large sample chamber 102 is used for targets with a large dynamic range in concentration. The sample 204 is between the light source (LED array 202, laser array, or single light source) and a CCD or CMOS image sensor 206. A filter 208 (e.g., a bandpass filter) can be inserted between the LED array 202 and the sample 204 to improve the temporal coherence of the LFHM 200. Some light is scattered by the sample 204, while most of the light is unperturbed, creating an in-line hologram at the plane of the image sensor 206.

The in-line hologram is recorded and reconstructed computationally (by an operably connected automated image processor (not shown)) to provide an image of the sample plane. In this instance, reconstruction is based on the ability to detect small particles. The ability to detect small particles depends primarily on the signal-to-noise ratio (SNR) of these particles in the final image relative to the background. While SNR can be enhanced through sample preparation techniques such as wetting films or nanolenses, computational methods can be applied with or without sample preparation enhancements. In addition to its SNR, the system's optical resolution also affects its ability to sense individual particles, especially when the spacing between objects is small. The resolution of a single LFHM image is limited by the pixel size of the image sensor, which is typically no smaller than ~1 μm, even with state-of-the-art color image sensors. A pixel super-resolution (PSR) technique can improve resolution and boost SNR by acquiring multiple images. Shifting or multiple light sources are utilized to illuminate a sample from slightly different angles so that multiple partially redundant low-resolution (LR) holograms are captured and used to synthesize a high-resolution (HR) hologram. Assisted by the PSR technique, the resolution of a LFHM is no longer limited by pixel size, and instead may be limited by diffraction, coherence, or hologram SNR.

Synthesizing a HR hologram from multiple partially redundant LR holograms can be treated as an optimization problem, where a regularized least-squares optimization routine can be used to estimate the HR hologram. Different regularization methods have been proposed to reduce noise in either the HR hologram or its reconstruction, including minimizing the variation in neighboring pixels, minimizing the high-frequency content of the hologram, minimizing the total variation in the reconstruction, optimizing for sparsity in the reconstruction after a basis transform, and optimizing for natural sparsity in the reconstruction. Despite these many studies of regularized optimization in holography, there is no definitive method that performs best in the specific case of small-target sensing, which is particularly relevant for practical bio-sensing applications of LFHMs.

A logical choice for reconstructing small targets with the best SNR and resolution is to optimize for natural sparsity in the reconstruction domain. Therefore, the following sparsity-promoting algorithm is used to boost SNR and thus, can be used detect small targets:

$$\hat{z} = \frac{\arg\min}{z} \left\{ \frac{1}{2} \sum_{m=1}^{pM} \left( s_m - \sum_{r=1}^{N} w_{m_1 r} z_r \right)^2 + \kappa \| |P(z;-d)| - B^2 \|_{l_1} \right\}$$

where $\hat{z}$ is the HR hologram estimate, z is the HR hologram, p is the number of LR holograms, M is the pixel number in LR holograms, m is the LR hologram pixel index, s is the LR holograms, r is the HR hologram pixel index, N is the pixel number in LR hologram, w is the projection coefficient, $z_r$ is the hologram pixel value, κ is the regularization weight, P is the back-propagation operator of light, d is the sample to sensor distance, B is the reconstructed field background brightness, and $l_1$ is the $l_1$ norm.

Figure 4:
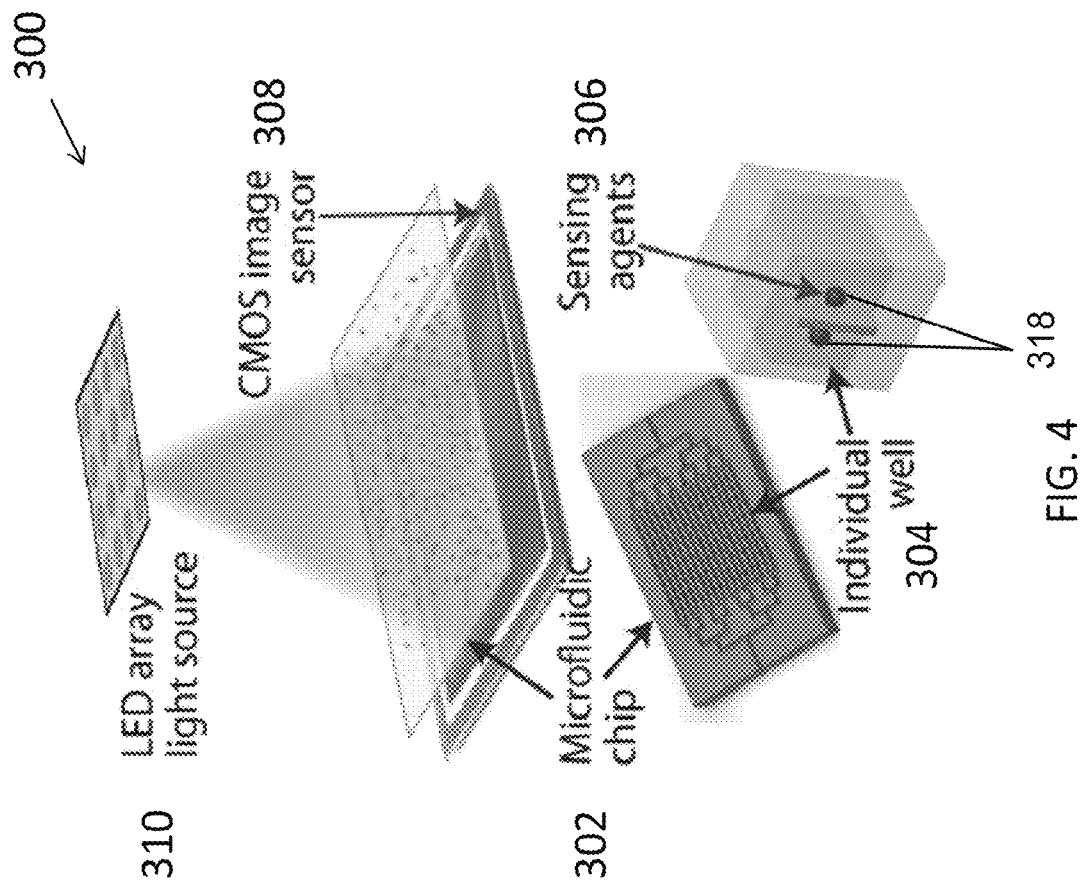
FIG. 4 is a diagrammatic representation of the components of a biosensor system, according to an embodiment.

Turning now to FIG. 4, there is shown a diagrammatic representation of the components of an embodiment of a biosensor system 300 (or "LFHM system," as used interchangeably herein). In the example shown in FIG. 4, the system 300 includes a microfluidic chip 302 with a plurality of small individual wells 304 and ports 306 to receive sensing agents. The microfluidic chip 302 may be composed of PDMS or any other similar suitable material. The microfluidic chip 302 can be fabricated in PDMS using a single-step molding procedure from a silicon/SU-8 master created using standard photolithography techniques with the open side of the PDMS chip 302 sealed using another thin PDMS layer. The entire chip 302 can be passivated using a polyethylene glycol (PEG) silane coating to prevent nonspecific binding and fouling of biomolecules to the surface of the chip. In an embodiment, the microfluidic chip 302 has ~$10^5$ wells 304 (or chambers).

The embodiment of the biosensor system 300 with a microfluidic chip 302 having a plurality of small individual wells 304 is used for multiplexed detection of targets. A stretchable microfluidic chip 302 can be used to create small chambers (e.g., wells 304) that lock beads, as shown in FIG. 2, inside. In an exemplary embodiment, a target analyte is "sandwiched" between two beads functionalized with antibodies in each well 304. Beads for different target biomarkers are localized within separate chambers (e.g., wells 304) within the microfluidic chip 302.

Figure 5:
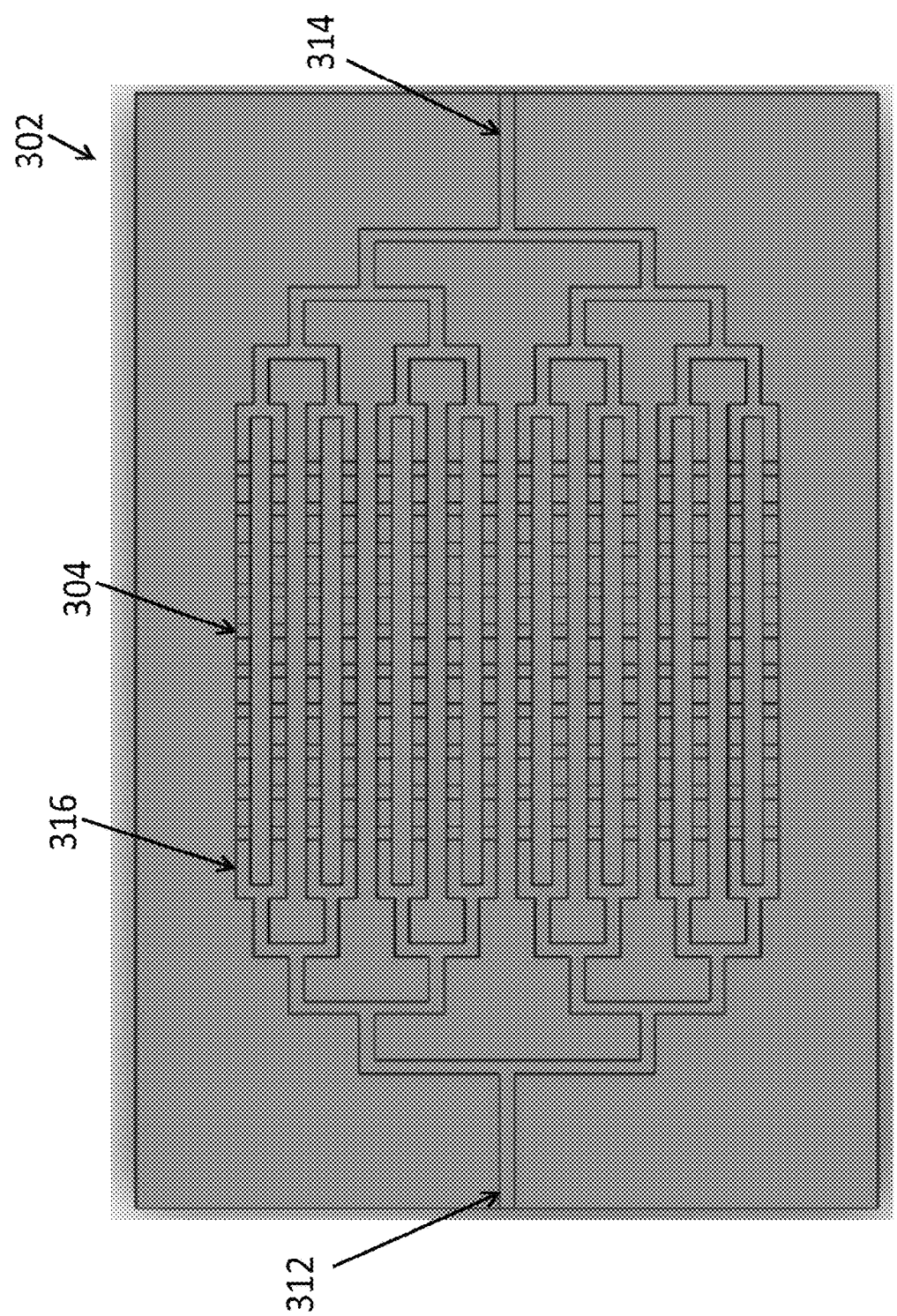
FIG. 5 is a top view schematic representation of the microfluidic chip, according to an exemplary embodiment.

An exemplary embodiment of the microfluidic chip 302 is shown in FIG. 5. The microfluidic chip 302 has a single inlet 310 and a single outlet 312. Between the inlet 310 and outlet 312, the chip 302 consists of a series of chambers (or wells 304) (15 μm×15 μm×5 μm) connected by channels 316. Freely floating within each chamber 304 are two, 1-μm diameter beads 318 (FIG. 4) functionalized with receptor molecules (e.g. antibodies) to bind to different physical regions of the same target. If the target has multiple binding configurations to a given receptor, then the same receptor molecules can be used on each bead 318 within the chamber 304. For example, in a biotin-NeutrAvidin interaction, the target (NeutrAvidin) and receptor (biotin) can bind in four different configurations. Therefore, the premise of the system 300 is that if the target analyte is present within that chamber 304, then both beads 318 will sandwich around the target molecule, indicating its presence.

In an exemplary embodiment, the microfluidic chip 302 has 230 parallel channels, each with 305 chambers (or wells 304), for $N_{tot}=7.015\times10^4$ total chambers, corresponding to a total sample volume of ~0.1 μL, which also takes into account the volume of the channels connecting the chambers (wells 304).

Figure 6A:
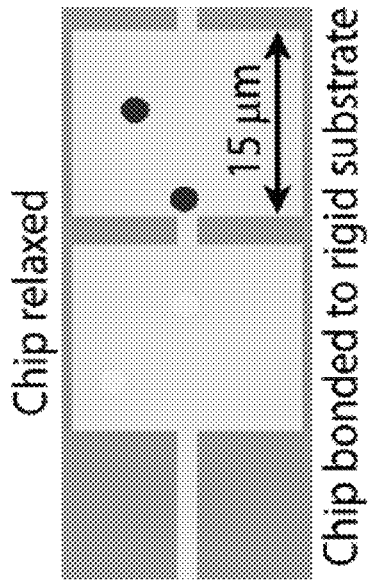
FIG. 6A is a schematic representation of an optical tweezer based chamber loading procedure, according to an embodiment.
Figure 6A:
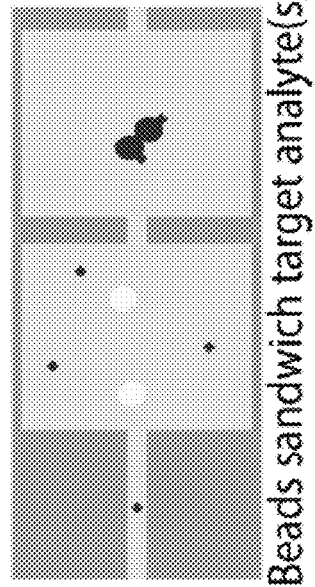
Figure 6A:
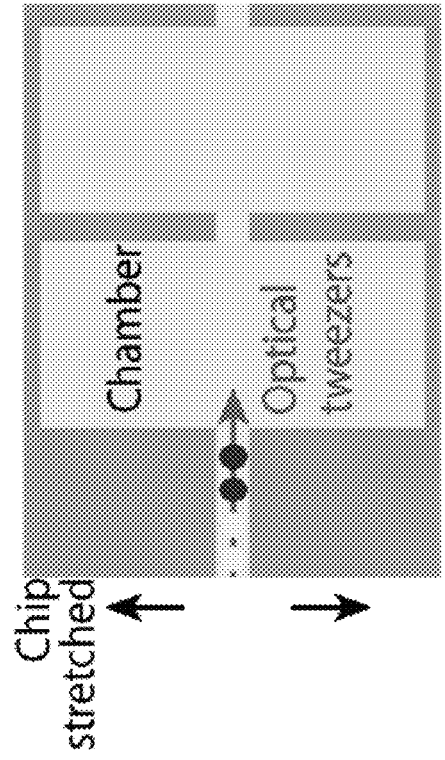
Figure 6A:
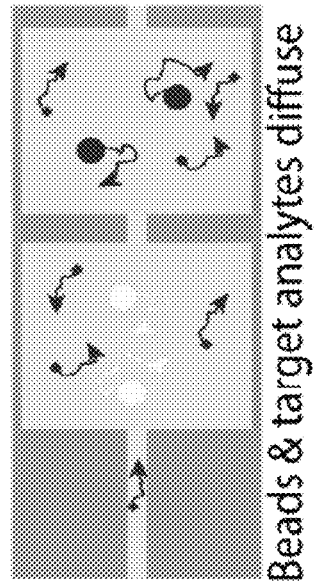

In a preferred embodiment, high speed computer-controlled optical tweezers are used to load functionalized beads 318 into wells 304 within the microfluidic chip 302, as shown in FIG. 6A. During loading, the flexible PDMS chip 302 will be stretched so that the channels 316 connecting the chambers 304 are wider than the beads 318. After loading, the PDMS chip 302 will be relaxed, locking the beads 318 in their chambers 304. The chip 302 will then be bonded to a rigid substrate before being delivered to the end user, who will flow a sample through the chip 302.

While clogging of the microchannels 316 is a potential issue, the risk is minimized, in this case. During chip loading, the optical tweezers will precisely guide individual particles through the centers of the channels 316. During sample testing, there are only two beads 318 per chamber (or well 304), which are not enough to clog the connecting channels 316. A surfactant can also be used in the solution, e.g., Tween, or passivation of the microfluidic chip 302 with PEG can be employed to prevent the particles from sticking to the walls of the channels 316 by van der Waals, electrostatic, or hydrophobic interactions. Alternatively, a perfluorocarbon passivation coating can be used instead of PEG.

In an embodiment, particle pairs are spaced ~20 μm apart on the chip 302, which corresponds to ~$1.4\times10^5$ beads per chip across a 28 mm² area (the active area of the image sensor). To position all of these particles, holographic optical tweezers are used that employ a spatial light modulator to generate ~100 trapping beams in parallel so that 100 beads can be positioned simultaneously. Assuming the average particle drag distance is 1 mm and the average manipulation speed is 2 mm/s, then $1.4 \times 10^5$ particles can be positioned in approximately 10 minutes.

Figure 6B:
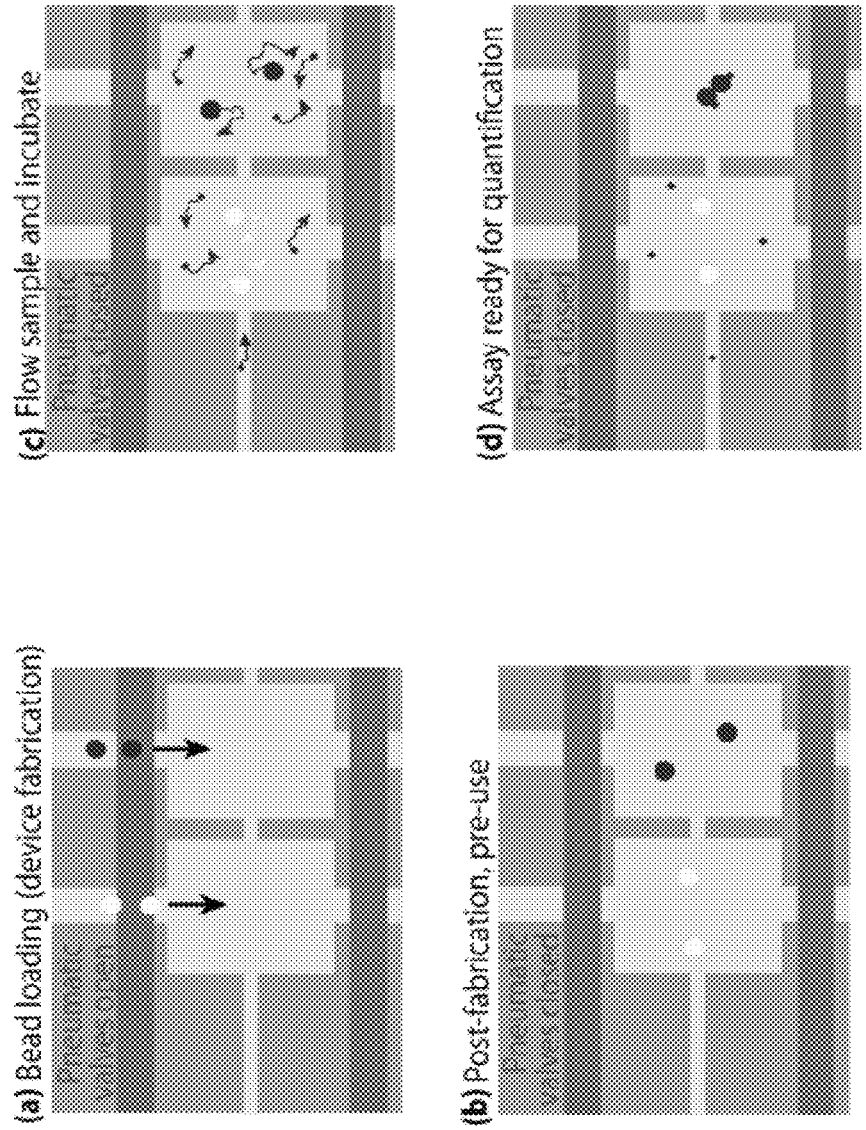
FIG. 6B is a schematic representation of a valve-based chamber loading procedure, according to an embodiment.

While the optical tweezer approach is reasonably fast for a research setting, it may be too slow for future large-scale manufacturing. In this case, the loading of the beads can be done entirely through microfluidics using valves, as shown in FIG. 6B. Microfluidic systems have been demonstrated that can precisely space beads flowing in microfluidic channels. These approaches can used to space beads such that the spacing between each pair of beads equals the vertical chamber pitch. This bead train will then flow through pneumatic valves, which will close once the beads are all in place. In comparison with the optical tweezer based approach, the valve-based approach will require a more complicated multilayer PDMS chip design, as well as more precise timing and valve automation. However, it can ultimately provide the high throughput necessary for mass fabrication. A hybrid approach may also be advantageous, where most of the beads are positioned using microfluidic flow, with optical tweezers only being used for error correction in case some beads were initially misplaced.

Referring back to the optical tweezer embodiment for loading the microfluidic chip, the precision of optical tweezers allows for the production of a microfluidic chip 302 with a corresponding "map" of how each bead is functionalized for which target. In other words, the well 304 locations and corresponding surface functionalizations are recorded to enable multiplexing during readout. When two beads are observed to sandwich an analyte, the map will be used during the readout to immediately know the analyte through the location of the bead pair within the field of view of the reader system. Ideally, the functionalized beads come from a different stock solution for each target. The loading of beads from many different stock solutions via optical tweezers thus enables a large degree of multiplexing within a single chip, where the maximum level of multiplexing would involve each bead-pair sensing for a different target.

As shown in FIG. 4, the microfluidic chip 302 holds the sample (sample 204 of FIG. 3) in the individual wells 304 between the CMOS image sensor 308 and the LED array 310 of the biosensor system 300 (LFHM). The LED array 310 illuminates the sample from different directions, generating multiple points of view. Such a biosensor system 300 also incorporates an operably connected automated imaging processor (not shown). A biosensor system 300 as shown in FIG. 4 has the capabilities to process (i.e., automatically measure) the binding rate of thousands of beads (in FIG. 2).

The biosensor system 300 does not directly capture an in-focus image of the sample. Instead, the biosensor system 300 captures an interference pattern between light transmitted straight through the transparent substrate and light that is scatter by objects on the substrate. This interference pattern constitutes an in-line hologram. The hologram can be computationally reconstructed to provide an in-focus image of the transparent sample. The resolution of this biosensor system 300 is often limited by the pixel size of the image sensor. To overcome this limitation, a pixel super-resolution (PSR) method that synthesizes a high-resolution image from multiple low-resolution images that come from different points of view can be used. After having computationally obtained the microscopic image of the microfluidic chip, standard image processing routines will be used to segment the image and identify the locations of beads. The bead positions are correlated with specific analyte targets to provide concentration levels. Objects such as channel walls and dust can be removed from the image through thresholding and measurements of object size. In a similar way, bound bead-pairs can be discriminated from individual beads based on their apparent sizes. The proposed image processing algorithm (stated above) will ultimately aggregate all of the binding data from the chambers with the known functionalities of the beads in each chamber to report concentration values with error bars to the user.

The above biosensor system 300 can be used to measure cancer-relevant biomarkers. For example, BTLA, GITR, HVEM, LAG-3, PD-1, PD-L1, PD-L2, and TIM-3 can be sensed.

Microscopic and/or nanoscopic beads suspended in an aqueous solution undergo Brownian motion, causing them to move randomly even without macroscopic flow. Therefore, there is a need for a high-speed imaging system to be able to resolve microscale (diameters<5 a high-speed imaging system can be used to resolve microscale (diameters<5 um) beads without significant motion blur. According to the methods discussed below, up to 16 raw frames can be captured at speeds between 15 and 30 frames per second of the sample, where each frame is acquired from sample illumination at a different angle using a different LED. Illumination of the sample from different angles is used to provide a higher resolution reconstructed image of the sample using pixel super-resolution discussed above.

Figure 7A:
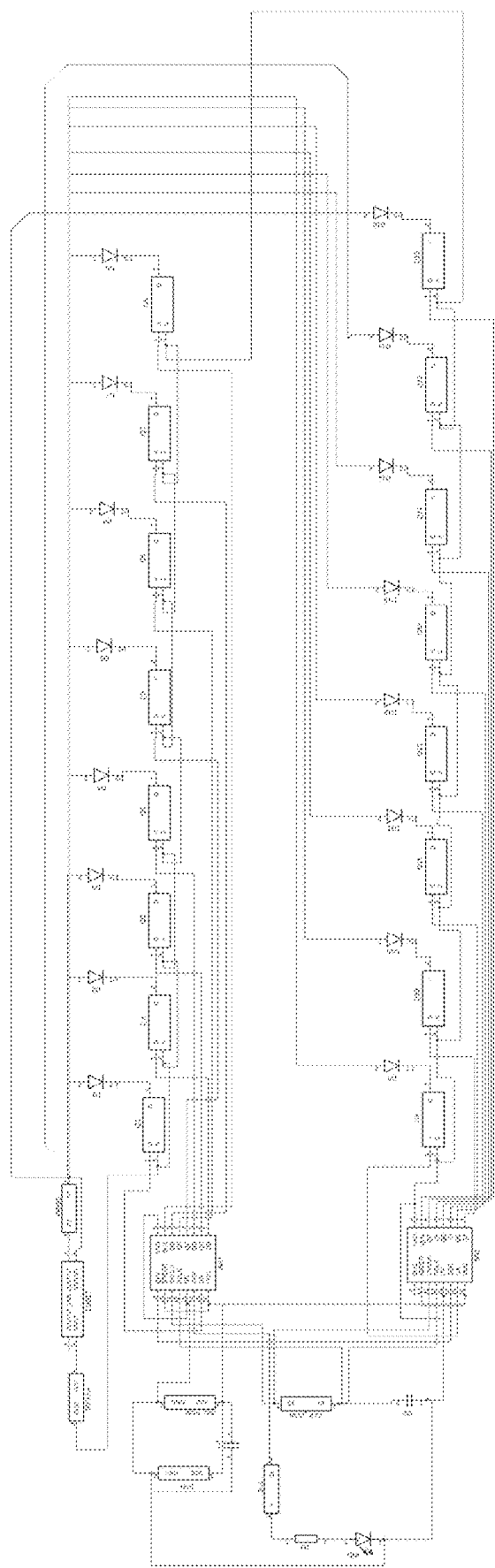
FIG. 7A is a schematic representation of an exemplary circuit layout.
Figure 7B:
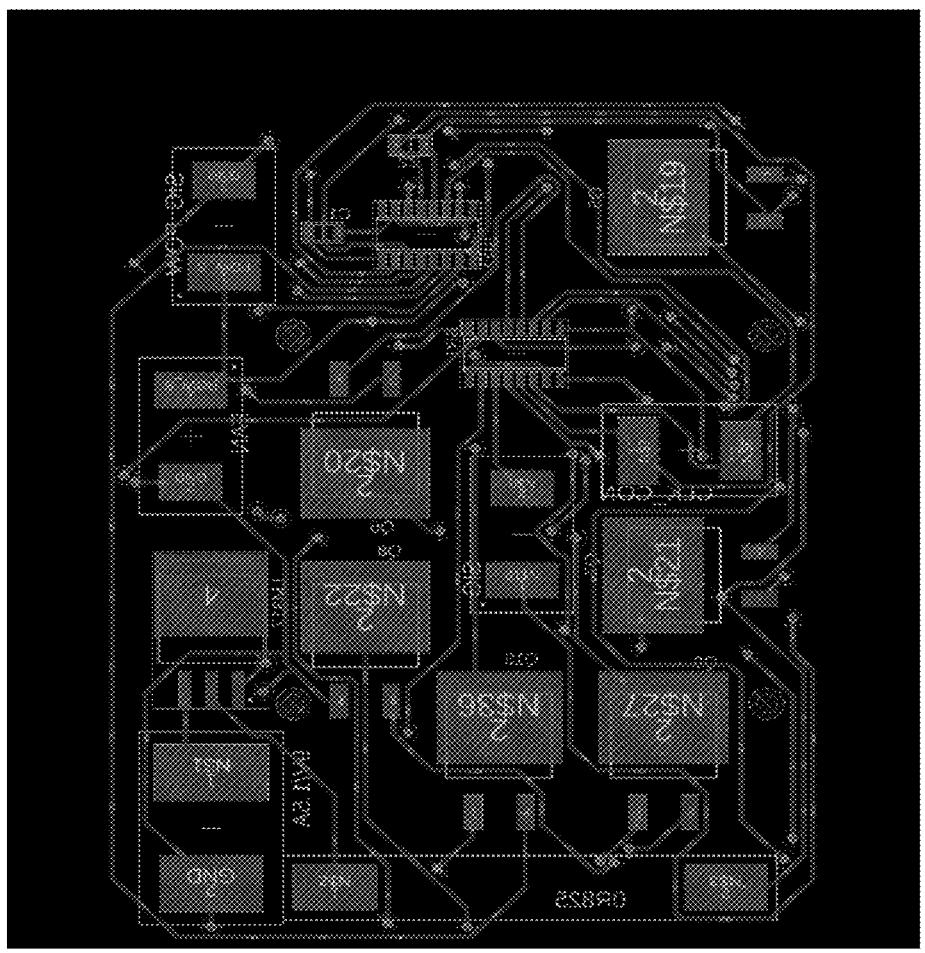
FIG. 7B is a schematic representation of a first side of a printed circuit board, according to an exemplary embodiment.
Figure 7C:
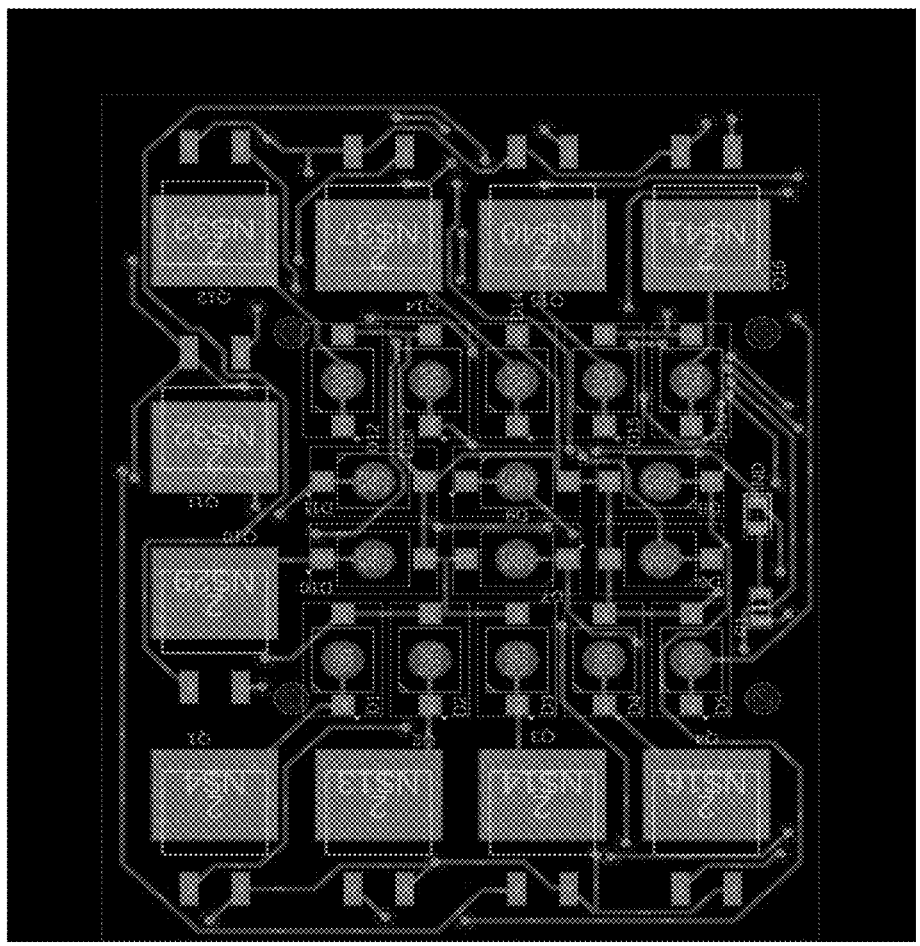
FIG. 7C is a schematic representation of a second side of a printed circuit board, according to an exemplary embodiment.

To achieve a high-speed multi-angle illumination system, an electronic board (FIG. 7A) is used to house and control the LEDs along with a computer program to control the timing. Another embodiment of the printed circuit board is shown in FIGS. 7B-7C. The electronic circuit board/printed circuit board can be generally termed an "electronic control system." The electronic control system is connected (via a wired or wireless connection) to the light source 202/310. The electronic control system is used to selectively turn on/off the light source (if a single light source) 202/310 or one or more light sources in a laser or LED array 202/310. By switching the light sources 202/310 on and off at high speeds while capturing images, the motion blur can be reduced. The timing of the switching can be programmed (via the computer program) for the electronic circuit board/printed circuit board.

In an exemplary embodiment, *E. coli* pathogens are sensed using the lens-free imaging system, utilizing it as a food safety sensor. Agglutination assays have been commonly used to detect viruses, bacteria, and abnormal red blood cells. An advantage of these tests is that full agglutination of the sample is visible to the unaided eye; however, the result is qualitative, and at low concentrations of the analyte, it can be difficult to identify only a handful of agglutinated pairs of beads. Previously, agglutination assays have been performed in microfluidic devices, where LODs as small as 10-100 cfu mL$^{-1}$ have been reported using Mie scattering to assess average particle size, which is a bulk measurement and does not measure individual particles or clusters. In methods described herein, sensitivity and specificity are optimized because small numbers of small clusters are individually counted and binding/unbinding is observed in real time.

While lens-free holographic microscopy has been applied to virus detection via agglutination, it has been performed on an open substrate as the solution was drying and relied extensively on laboratory-based instrumentation. By performing the assay in a well-controlled microfluidic environment with a larger number of functionalized beads, error bars can be significantly reduced, dynamic range can be enhanced, and the approach to the detection of food pathogens at low concentrations in solution can be extended, all in a field-portable device. While bead-based assays have been previously used in many other different sensing configurations, the method described herein is significantly unique in its ability to image and enumerate anywhere from a single bead-pair up to ~$10^5$ bead pairs.

Figure 8:
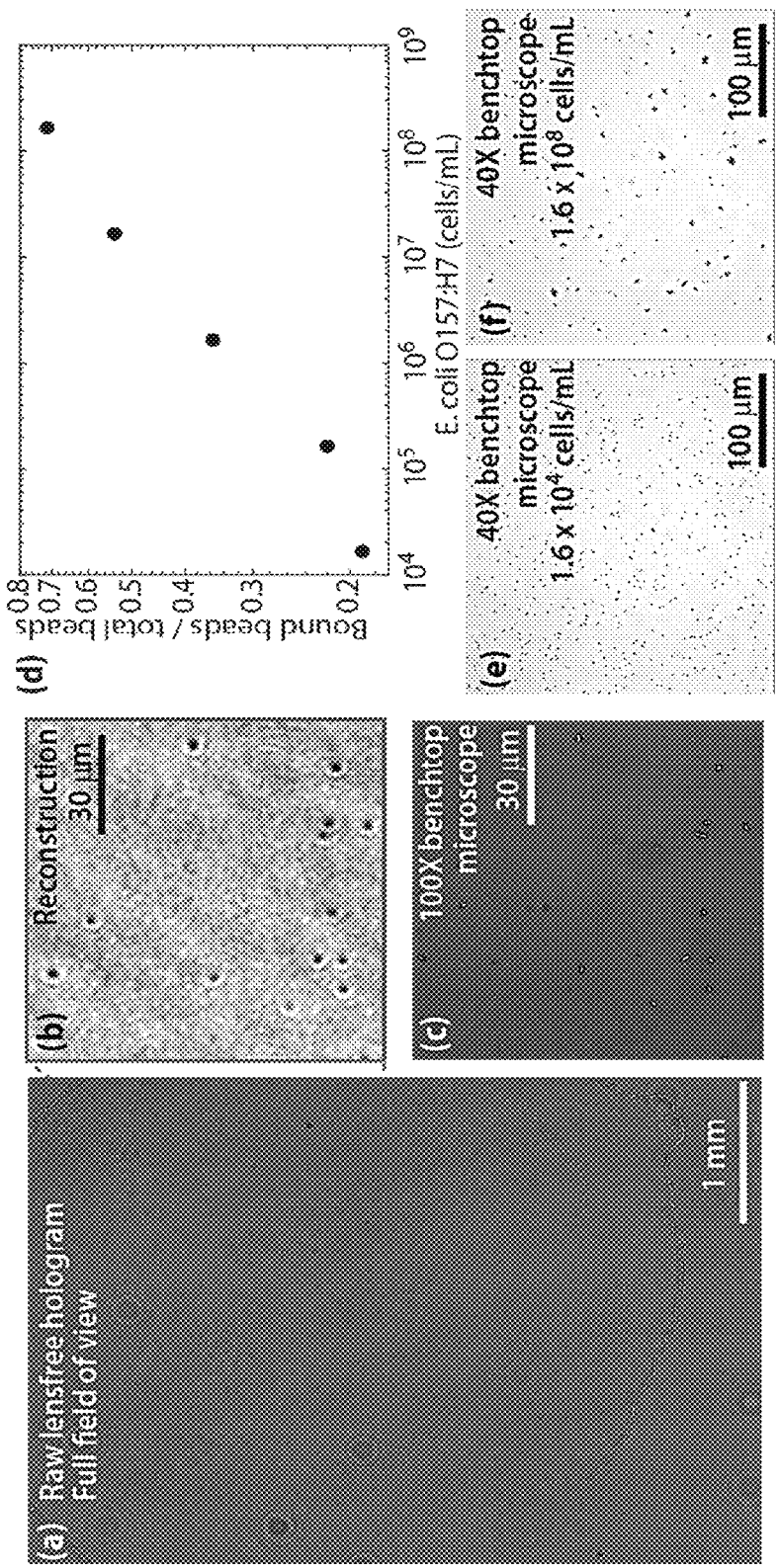
FIG. 8 shows experimental images of *E. coli* O157:H7 detection using the biosensor system.

Quantitative agglutination is used to measure *E. coli* O157:H7 concentrations. Agglutination is measured at cell concentrations as low as $1.6 \times 10^4$ cells/mL using images acquired with a conventional benchtop microscope. Using the disclosed system, which incorporates a microfluidic chamber and lens-free microscope, significantly lower LODs are achieved by measuring very large numbers of beads and the effects of nonspecific binding are minimized. FIG. 8 shows experimental images of *E. coli* O157:H7 detection using the disclosed biosensor system. Image (a) shows the raw hologram captured with the bionsensor system. Image (b) shows a small region of interest (ROI) of the reconstruction showing the direct imaging of formalin-killed *E. coli* O157:H7 cells. Image (c) compares the image of the same ROI taken with a benchtop microscope. Image (d) shows the beads counted using a benchtop microscope. (*E. coli* O157:H7 is sensed using beads functionalized with anti-O157 antibodies). (Images (e) and (f) of FIG. 8 are the images used to obtain the data plotted in image (d)).

In another exemplary embodiment, biotin-coated beads are used to sense individual NeutrAvidin (NAv) protein molecules. Free NAv are mixed with biotin-coated beads and the solution is imaged in a benchtop microscope. Free NAv are used because: (1) the biotin-NAv bond is stable and robust; (2) biotin-coated beads can be directly purchased; and (3) NAv is relatively inexpensive. Biotin-coated beads bind together when exposed to free NAv molecules. Because a single NAv molecule binds strongly to multiple biotin groups, bead clusters form, where the amount of clustering depends on the NAv concentration.

Figure 9:
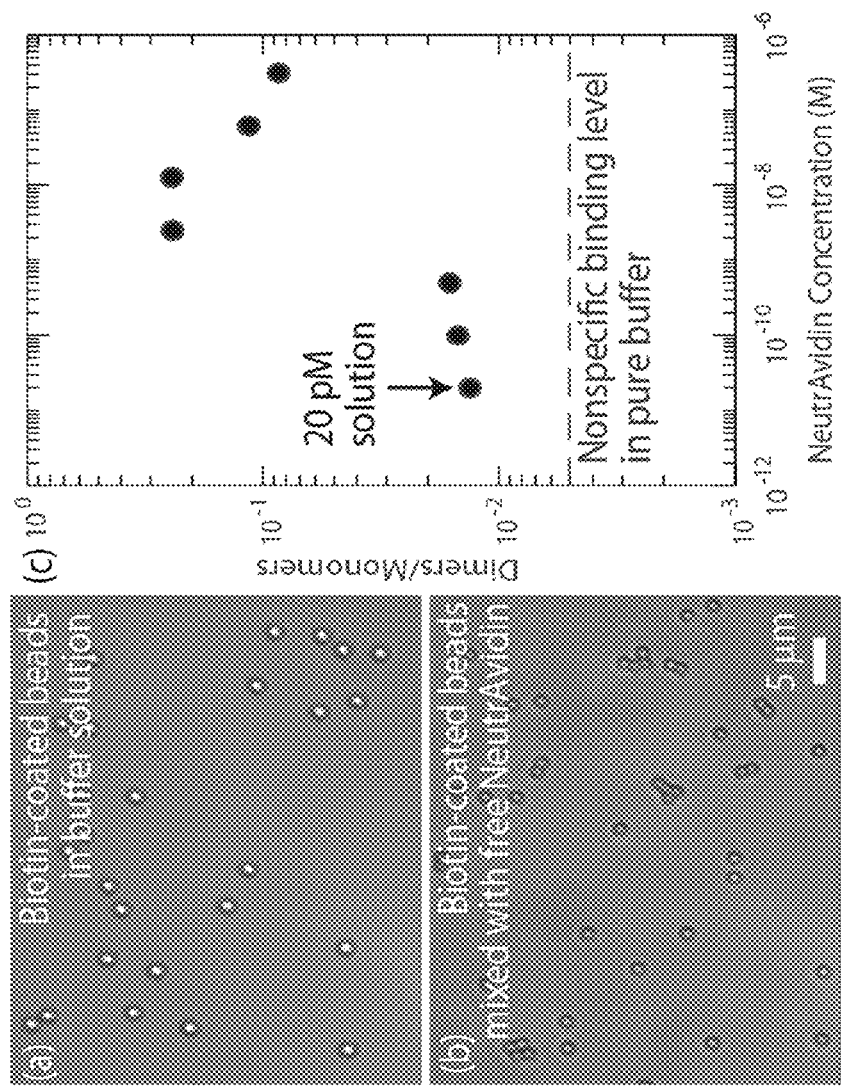
FIG. 9 is shows experimental images of the binding of functionalized beads to the target captured using the biosensor system.

FIG. 9 shows the binding of functionalized beads in the presence of a target analyte. Image (a) shows the Biotin coated beads in phosphate-buffered saline do not spontaneously bind to each other. Image (b) shows the same beads binding to each other when introduced to free NeutrAvidin, indicating the presence of the analyte. Image (c) shows that the ratio of dimer clusters to monomers varies with NeutrAvidin concentration, with a limit of a detection less than 20 pM. Note that at extremely high concentrations, free NAv molecules can completely coat the beads, effectively passivating them so that there is less agglutination. This data indicates a limit of detection somewhere below 20 pM. Also note that this curve is not particularly smooth due to two factors, neither of which would exist in the proposed lens-free imaging system: out-of-focus features can be mischaracterized and the "coffee-stain effect" can lead to spurious clusters.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An imaging system for the detection of a target, comprising:
 a lens-free holographic microscope comprising a light source in a first plane spaced above an image sensor;
 wherein the image sensor extends in a second plane;
 a microfluidic chip positioned between the light source and the image sensor;
 wherein the microfluidic chip extends in a third plane, which is parallel to the second plane;
 at least one chamber in the microfluidic chip configured to receive a sample solution comprising a target; and a plurality of functionalized beads, any two of the plurality of functionalized beads with an affinity for binding together when exposed to the target in the sample solution;

wherein the plurality of functionalized beads are positioned within the at least one chamber in the microfluidic chip.

2. The imaging system of claim 1, wherein the at least one chamber is a plurality of wells.

3. The imaging system of claim 1, wherein the microfluidic chip is composed of a flexible, stretchable material.

4. The imaging system of claim 1, wherein the target is at least one of pathogens, protein molecules, DNA, or RNA.

5. The imaging system of claim 1, wherein the light source is an LED array.

6. The imaging system of claim 1, wherein the light source is a laser array.

7. The imaging system of claim 1, wherein the light source is a single light source.

8. The imaging system of claim 1, wherein the image sensor is a CCD image sensor.

9. The imaging system of claim 1, wherein the image sensor is a CMOS image sensor.

10. The imaging system of claim 1, wherein the functionalized beads are beads are either spherical or nonspherical.

11. The imaging system of claim 1, wherein the functionalized beads are composed of either dielectric materials or metals.

12. The imaging system of claim 1, wherein the functionalized beads are functionalized using one or more of the following capture agents: antibodies, protein aptamers, DNA aptamers, and RNA aptamers.

13. A method for determining the presence of a target in a sample, comprising the steps of:

providing an imaging system including a lens-free holographic microscope comprising a light source in a first plane spaced above an image sensor, wherein the image sensor extends in a second plane, a microfluidic chip positioned between the light source and the image sensor, wherein the microfluidic chip extends in a third plane, which is parallel to the second plane, at least one chamber in the microfluidic chip, and a plurality of functionalized beads, any two of the plurality of functionalized beads with an affinity for binding together when exposed to the target, wherein the plurality of functionalized beads are positioned within the at least one chamber in the microfluidic chip;

adding the sample to the at least one chamber in the microfluidic chip;

directing the light source toward the microfluidic chip and the image sensor;

capturing, via the image sensor, an interference pattern generated by light scattered by the sample;

generating a hologram image based on the interference pattern; and reconstructing the hologram image to generate an in-focus image.

14. The method of claim 13, wherein the step of reconstructing the hologram image to generate an in-focus image is based at least in part on the signal-to-noise ratio (SNR) of the target.

15. The method of claim 13, wherein the step of reconstructing the hologram image to generate an in-focus image is based at least in part on pixel super-resolution (PSR).

16. The method of claim 13, further comprising the steps of:

providing an electronic control system connected to the light source; and illuminating the light source selectively using the electronic control system, reducing motion blur of the in-focus image.

17. The method of claim 13, further comprising the step of measuring binding kinetics of the functionalized beads.

18. The method of claim 13, determining, from the in-focus image, the presence of one or more clusters of functionalized beads.

19. The method of claim 18, determining, from the in-focus image, the number of functionalized beads in each cluster in the in-focus image.

20. The method of claim 19, determining, from the in-focus image, the concentration of the target in the sample.

* * * * *